United States Patent
Köhler et al.

(10) Patent No.: US 10,131,617 B2
(45) Date of Patent: Nov. 20, 2018

(54) METHOD FOR PRODUCING DIARYL CARBONATES

(71) Applicant: Covestro Deutschland AG, Leverkusen (DE)

(72) Inventors: Karl-Heinz Köhler, Aachen-Brand (DE); Ricarda Leiberich, Neu-Isenburg (DE); Kaspar Hallenberger, Leverkusen (DE); Korbinian Krämer, Köln (DE); Florian Lipski, Ratingen (DE); Henning Kahnis, Köln (DE); Gabriel Denecker, Kalmthout (BE); Johan Vanden Eynde, Zwijnaarde (BE); Weerachanan Somhom, Uttaradit (TH)

(73) Assignee: COVESTRO DEUTSCHLAND AG, Leverkusen (DE)

( * ) Notice: Subject to any disclaimer, the term of this patent is extended or adjusted under 35 U.S.C. 154(b) by 3 days.

(21) Appl. No.: 15/308,983

(22) PCT Filed: May 4, 2015

(86) PCT No.: PCT/EP2015/059656
§ 371 (c)(1),
(2) Date: Nov. 4, 2016

(87) PCT Pub. No.: WO2015/169720
PCT Pub. Date: Nov. 12, 2015

(65) Prior Publication Data
US 2017/0073300 A1    Mar. 16, 2017

(30) Foreign Application Priority Data
May 9, 2014 (EP) .................... 14167762

(51) Int. Cl.
*C07C 68/08* (2006.01)
*C07C 68/02* (2006.01)

(52) U.S. Cl.
CPC .............. *C07C 68/08* (2013.01); *C07C 68/02* (2013.01); *Y02P 20/582* (2015.11)

(58) Field of Classification Search
None
See application file for complete search history.

(56) References Cited

U.S. PATENT DOCUMENTS 5,965,472 A    10/1999    Buysch et al.

FOREIGN PATENT DOCUMENTS

| EP | 1234845 A2 | 8/2002 |
| JP | 2001-131123 A | 5/2001 |
| WO | WO-2013-007601 A1 | 1/2013 |
| WO | WO-2015-169775 A1 | 11/2015 |

OTHER PUBLICATIONS

International Search Report and Written Opinion for International Application No. PCT/EP2015/059656, European Patent Office, dated Jul. 10, 2015.
International Search Report and Written Opinion for International Application No. PCT/EP2015/059774, European Patent Office, dated Jul. 6, 2015.

*Primary Examiner* — Samantha L Shterengarts
(74) *Attorney, Agent, or Firm* — K&L Gates LLP (57) ABSTRACT

The invention concerns a method for producing diaryl carbonates from monophenols and phosgene or chloroformic acid aryl esters in the presence of at least one optionally substituted pyridine or the hydrochloride salt thereof as catalyst, and the recovery and reinjection thereof back into the method. The method is carried out at least partially in a liquid phase without the use of an additional solvent, the catalyst being separated by means of distillation and recovered.

11 Claims, 2 Drawing Sheets

METHOD FOR PRODUCING DIARYL CARBONATES

CROSS-REFERENCE TO RELATED APPLICATIONS

This application is a U.S. national stage application, filed under 35 U.S.C. § 371, of PCT/EP2015/059656, which was filed on May 4, 2015, and which claims priority to European Patent Application No. EP 14167762.5, which was filed on May 9, 2014, the contents of each of which are incorporated by reference into this specification.

FIELD OF THE INVENTION

The invention relates to a process for preparing diaryl carbonates from monophenols and phosgene or aryl chloroformates in the presence of at least one optionally substituted pyridine or hydrochloride salt thereof as catalyst, and the recovery and recirculation thereof into the process. The process is carried out at least partly in the liquid phase without use of additional solvents, with the catalyst being separated off and recovered by means of a distillation.

BACKGROUND OF THE INVENTION

Processes for preparing pure diaryl carbonates from monophenols and phosgene are known. The preparation of diaryl carbonates (e.g. diphenyl carbonate, "DPC") is usually carried out by means of a continuous process, by preparation of phosgene and subsequent reaction of monophenols and phosgene in an inert solvent in the presence of alkali and a nitrogen catalyst in the interface.

The preparation of diaryl carbonates by, for example, the phase interface process is described in principle in the literature, see, for example, in Chemistry and Physics of Polycarbonates, Polymer Reviews, H. Schnell, Vol. 9, John Wiley and Sons, Inc. (1964), pp. 50/51.

In the phase interface process, the starter materials dissolved in solvents and water are reacted with one another. The disadvantage of these processes is the separation of the diaryl carbonate from the solvent by distillation and the renewed working up thereof, and also the sodium chloride-containing aqueous phase as waste product, for which there are only limited possible uses and which may require very complicated work-up steps.

For this reason, processes for the direct phosgenation of monophenols, in which the starting materials phosgene and monophenol are reacted not in a phase interface process in the presence of alkali metal hydroxide solution but in the melt in the presence of catalysts, preferably without use of additional solvents, to form diaryl carbonates and hydrogen chloride instead of sodium chloride, have been developed.

Thus, for example, U.S. Pat. No. 2,362,865 (A) describes a process for preparing diaryl carbonates by direct phosgenation of monophenols at temperatures of from 170° C. to 250° C. using Al phenoxides or Ti phenoxides, but no recirculation of the catalyst, nor is a separation method described.

Both EP 2 371 806 A and EP 2 371 807 A likewise describe processes for preparing diaryl carbonates by direct phosgenation of monophenols at temperatures of from 20° C. to 240° C. using metal halides or metal phenoxides. Recirculation of the catalyst into the process has likewise not been described.

EP 1 234 845 A likewise describes the reaction of monophenols in the melt at temperatures of from 120° C. to 190° C. with a particularly pure phosgene. Nitrogen-containing compounds, e.g. pyridine in amounts of from 0.1 to 10 mol %, based on monophenol used, are employed as catalysts. This publication, too, gives no indication of recirculation of catalyst into the process. Pyridine forms a relatively non-volatile salt (boiling point: 222-224° C.) with hydrogen chloride and this cannot be distilled off readily. According to the teaching of EP 1 234 845 A, the reaction mixture is therefore firstly neutralized with sodium hydroxide, so that a mixture of water, free pyridine and excess phenol can be distilled off.

WO 2011007001 describes the desublimation of pyridine hydrochloride from a reaction mixture. For this purpose, dichlorosilane-pyridine adduct is heated to 200° C. in a full oil pump vacuum, with pyridine hydrochloride being volatilized and precipitating as a solid.

In addition, there are a number of further patents such as WO 2008/114750 A1, JP 2008-231073 A, JP 2009-114195 A, JP 09-278714 A, JP 09-100256 A, JP 10-245366 A, JP 11-012230 A in which the reaction of monophenols in the melt with phosgene to form diaryl carbonates in the presence of homogeneously soluble nitrogen-containing catalyst is described.

JP 10-077250 A, JP 09-24278 A and EP 1 234 845 A refer to possible recirculation of catalyst, but without making mention of a specific separation of catalyst from the product and a work-up method for the catalyst with a view to recirculation thereof. In addition, reference is made to introduction of aqueous solutions, in particular water and/or sodium hydroxide solution, during the course of neutralization and washing of the reaction mixture.

U.S. Pat. No. 5,239,106 teaches the separation of diphenyl carbonate from catalyst-containing reaction solutions by crystallization of the 1:1 adduct with phenol. However, isolation and recirculation of catalyst is not described here.

None of these publications provide satisfactory indications of methods for recirculation of the catalyst, e.g. pyridine, into the process. In particular, the catalyst is separated off via the aqueous phase after a neutralization step using an aqueous, alkaline solution.

In particular, the prior art does not give any concrete examples of a process for separating the catalyst from the product-containing stream, in which neutralization of the hydrochloride by means of water-containing additions, which is encumbered by the above-described disadvantages, is not carried out as in the above-cited documents.

None of these publications describes a completely water- and wastewater-free process for preparing diaryl carbonates.

The processes known from the prior art are therefore not able to satisfy the demanding economic and ecological requirements in respect of catalyst recirculation and additionally ensure high purities of the products, which in turn are starting materials for further chemical processes.

However, economic aspects have to be taken into account for an industrial process. Recirculation of the catalyst is among the important aspects which are assessed at this point, since a high degree or complete discharge of the catalyst means an economic disadvantage and leads to undesirable pollution of the environment. The wastewater formed has to be purified with a very high outlay, which represents a great challenge for the water treatment works. In the processes of the prior art, either a high technical outlay is necessary in order to make recirculation of the catalyst possible or partial or complete discharge of the catalyst is provided. In both cases, an additional wastewater stream is provided.

In a direct phosgenation process, the provision of efficient recirculation of the catalyst is of the highest importance. Furthermore, the use of aqueous solutions should be avoided wherever possible, not only during the reaction but also in the work-up. This is because wastewater containing organic substances firstly has to be purified in a complicated fashion and then be disposed of.

SUMMARY OF THE INVENTION

It is therefore a technical objective to develop a process for preparing diaryl carbonates by the direct phosgenation process in the melt of a monophenol with omission of additional starting materials such as sodium hydroxide and water, which process is operated economically by reducing discharge of streams (purge) and provides a constant good quality of the end products.

It has now surprisingly been found that when an optionally substituted pyridine or a salt thereof is used as catalyst, the hydrochloride salt formed, the hydrogen chloride and the diphenyl carbonate can be separated from one another by distillation and a diaryl carbonate of high purity can be obtained. Surprisingly, no desublimation of the pyridine hydrochloride salt occurs during the distillation operation, since the salt remains dissolved in the low boiler phase separated off and forms a liquid mixture with phenol even at room temperature.

Neutralization of the reaction solutions or mother liquor and/or the addition of water are preferably dispensed with. This leads to a particularly economical and ecological process.

DETAILED DESCRIPTION OF THE INVENTION

The invention accordingly provides a process for preparing diaryl carbonate, preferably diphenyl carbonate, by reaction of at least one monophenol with phosgene and/or at least one aryl chloroformate in the presence of at least one optionally substituted pyridine, in free form and/or in the form of the hydrochloride salt thereof, as catalyst, wherein
  a) the reaction is carried out in a reactor under pressures of 1-50 bar (absolute),
  b) the reaction mixture is transferred from the reactor into a single-stage or multistage distillation apparatus,
  c) a catalyst-containing distillate is separated off at the top of at least one distillation column,
  d) the catalyst-containing distillate is at least partly recirculated into the reactor of step a),
  e) diaryl carbonate is separated off via a side stream from the column and is optionally purified further.

An aqueous solution is preferably not used in any of the steps a) to e).

The reaction in step a) is preferably carried out at temperatures above 80° C. in order to avoid precipitation of resulting diaryl carbonate in solid form. The reaction of the starting materials can be carried out either at atmospheric pressure or slightly reduced pressure or else at elevated pressures of up to 50 bar (absolute). Here, depending on the process conditions, the phosgene can be present in the condensed phase or be dissolved in the liquid phase. The diaryl carbonates prepared by this process are, owing to their high purity, particularly suitable for preparing high-purity polycarbonates from diaryl carbonates and bisphenols by the melt transesterification process.

The hydrogen chloride obtained in the reaction can be subjected to one or more purification steps so that it is suitable for many further possible uses, in particular for electrochemical or thermal oxidation to form chlorine. This chlorine obtained in this way can be reacted with carbon monoxide to produce phosgene; the phosgene obtained can be used in the process of the invention.

The end product, which is liquid under the reaction conditions, is separated from by-products and the catalyst or the HCl adduct thereof in a plurality of separation steps comprising the steps b), c) and e). It then preferably has a content of more than 95%, preferably more than 99.0%, particularly preferably more than 99.5%, of diaryl carbonate and possibly phenol. The end product preferably comprises mostly diaryl carbonate. The catalyst used in the reaction is worked up in such a way that it can be at least partly recirculated to the reaction (step d)).

The process of the invention consists of the three process sections:
  I. reaction comprising the process step a),
  II. hydrogen chloride work-up (optional),
  III. product purification and catalyst isolation by distillation comprising the process steps b), c) and e), with the recovered catalyst being at least partly recirculated to section I. (step d)).

In process section I), viz. reaction, the starting materials are mixed with one another in a preceding process step in such a way that a largely homogeneous solution of phosgene in the molten monophenol is present; this can optionally be effected by use of elevated pressures at the prescribed melt temperatures.

Diaryl carbonates prepared in the context of the invention are preferably those of the general formula (I)

where R, R' and R" can each be, independently of one another, hydrogen, halogen or a branched or unbranched $C_1$-$C_9$-alkyl radical or a branched or unbranched $C_1$-$C_9$-alkoxycarbonyl radical. R, R' and R" are preferably the same on both sides of the formula (I).

Particular preference is given to diphenyl carbonate.

Monophenols which are suitable for the purposes of the invention are preferably those of the general formula (II)

where R, R' and R" can each, independently of one another, have the meaning indicated for the general formula (I).

For the purposes of the invention, "$C_1$-$C_4$-alkyl" is, for example, methyl, ethyl, n-propyl, isopropyl, n-butyl, sec-butyl, tert-butyl; "$C_1$-$C_6$-alkyl" is additionally, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl or 1-ethyl-2-methylpropyl; "$C_1$-$C_9$-alkyl" is additionally, for example, n-heptyl or n-octyl or n-nonyl. The same applies to the corresponding alkyl radical in alkylcarbonyl radicals.

Suitable monophenols are, for example: phenol, alkylphenols such as cresols, p-tert-butylphenol, p-cumylphenol, p-n-octylphenol, p-isooctylphenol, p-n-nonylphenol and p-isononylphenol, halophenols such as p-chlorophenol, 2,4-dichlorophenol, p-bromophenol, 2,4,6-tribromophenol, anisole and methyl or phenyl salicylate.

Particular preference is given to phenol.

The monophenols used should have a purity of at least 99.90% by weight.

The starting materials preferably contain less than 300 ppm by volume of water since the presence of water promotes corrosion of the materials of the apparatus.

The monophenol used here can contain not only the phenol introduced from outside into the overall process, viz. the fresh phenol from stock tanks, but also recirculated monophenol from condensate streams from process steps II) and III) or from washing liquid streams from process step II). Monophenol which has been recirculated in this way can contain by-products from the process, e.g. residual amounts of diaryl carbonate, hydrogen chloride or aryl esters of chlorocarbonic acid, which are not damaging to the reaction. The monophenol is preferably present in more than the stoichiometrically required amount based on phosgene in the mixture of starting materials used. The molar ratio of monophenol to phosgene can vary in the range from 1.5:1 to 4:1, with preference being given to a molar ratio of from 2:1 to 3:1 and particular preference being given to a molar ratio of from 2.5:1 to 3:1.

In the following, the term "aryl chloroformate" is used to refer to compounds which are formed as intermediate in the preparation of diaryl carbonates from monophenols and phosgene.

Aryl chloroformates which are suitable for the purposes of the invention are preferably those of the general formula (III)

where R, R' and R" can each have, independently of one another, the meaning indicated for the general formula (I).

When an aryl chloroformate of the general formula (III) is reacted with a monophenol of the general formula (II), R, R' and R" each preferably have the same meaning in the formulae (I) and (II).

Particular preference is given to phenyl chloroformate.

To avoid undesirable by-products in the end products of the production process, the phosgene used should have a purity of at least 99.80% by weight, preferably 99.96% by weight; the content of carbon tetrachloride should be less than 50 ppm by volume, preferably less than 15 ppm by volume.

According to the invention, a substituted or unsubstituted pyridine is used as catalyst. This can be present in the form of a free base or entirely or partially in the form of its hydrochloride. "In the form of the free base" or "in free form" means, for the purposes of the invention, that the nitrogen of the pyridine ring is not present in protonated form.

Preference is given to not more than 10 mol %, particularly preferably not more than 1 mol %, of the optionally substituted pyridine being present in free form. The remainder is present in the form of the hydrochloride.

The pyridines serving as catalyst according to the invention are preferably those of the general formula (IV)

where $R^1$ and $R^2$ can each be, independently of one another, H, branched or unbranched $C_1$-$C_9$-alkyl, $C_5$- or $C_6$-cycloalkyl, OH, $OR^3$, $NHR^3$ or $NR^3R^4$, where $R^3$ and $R^4$ are each, independently of one another, $C_1$-$C_4$-alkyl. Particular preference is given to $R^1$ and $R^2$ being H.

Suitable pyridines are, for example, pyridine, 2-picoline, 3-picoline, 4-picoline, 2-ethylpyridine, 3-ethylpyridine, 4-ethylpyridine, 2-isopropylpyridine, 3-isopropylpyridine, 4-isopropylpyridine, 2-butylpyridine, 4-tert-butylpyridine, 2,3-lutidine, 2,4-lutidine, 2,5-lutidine, 2,6-lutidine, 3,4-lutidine, 3,5-lutidine, 3,4-diethylpyridine, 3,5-diethylpyridine, 3-ethyl-4-methylpyridine, 2-(3-pentyl)pyridine, 4-(3-pentyl) pyridine, 2-dimethylaminopyridine, 4-dimethylaminopyridine, 2-methoxypyridine, 2,6-dimethoxypyridine, 4-cyclohexylpyridine, 4-(5-nonyl)pyridine, 4-phenylpropylpyridine and 2-hydroxypyridine.

Particular preference is given to pyridine.

In a particularly preferred embodiment, the catalyst is pyridine hydrochloride.

The catalysts to be used according to the invention can be used in amounts of from 0.001 mol % to 10 mol %, preferably in amounts of from 0.01 mol % to 5 mol %, based on monophenol present.

The catalysts are used as a solution in the monophenol melt. Such solutions contain, according to the invention, at least some amounts of catalyst which are recirculated from process section III), with or without separate catalyst work-up, into the reaction in process section I). A catalyst work-up is therefore not absolutely necessary but quite possible for the recirculation of the catalyst into process section I).

The addition of the catalysts is carried out at the earliest after complete mixing of the starting materials, preferably in the reactor, in order to avoid premature reaction of the starting materials during mixing and thus premature evolution of hydrogen chloride in an unsuitable process section.

Recirculation of amounts of catalyst from the process section III) can be carried out as frequently as desired; in continuous processes, a partial amount of the catalyst can preferably be recirculated continuously while a partial amount is optionally discharged from the process circuit in order to prevent contamination of the catalyst or possibly to take into account deactivation of the catalyst. Fresh catalyst can be added to the recirculated amount of catalyst when necessary. In a preferred embodiment, at least 25% by weight of the catalyst, particularly preferably at least 50% by weight, very particularly preferably at least 75% by weight and in particular at least 85% by weight, is recirculated. However, in a preferred embodiment, not more than 99% by weight of the catalyst, preferably not more than 95% by weight, is recirculated.

The starting materials monophenol and phosgene are mixed with one another in the molar ratios indicated above or in the abovementioned preferred molar ratios, with the monophenol always being present as melt and the phosgene being gaseous or liquid, depending on the prevailing pressure. At atmospheric pressure and temperatures above 60° C., a two-phase gas/liquid mixture is largely present since the solubility of phosgene also decreases with increasing temperature in monophenols as also in diaryl carbonates.

For this reason, mixtures of molten monophenols and phosgene have to be very intensively mixed and redispersed in the reaction phase in order to ensure sufficient reaction of the starting materials by means of satisfactory replenishment of the phase interfaces. As an alternative, the reaction of phosgene with phenol can be significantly increased in a condensed homogeneous phase (owing to the increased concentration of phosgene in the phenol compared to the two-phase mixture of gaseous phosgene and liquid phenol). Increasing the temperature also has an accelerating effect on the reaction rate, so that elevated temperatures in the range from 100° C. to 250° C., preferably from 110° C. to 220° C., can be advantageous. However, since temperatures as mentioned above reduce the solubility of phosgene in phenol, carrying out the reaction at elevated temperature under superatmospheric pressure is particularly advantageous. For this reason, the starting materials are mixed with one another and reacted at elevated temperature under atmospheric pressure, preferably under an elevated pressure up to 50 bar (absolute), particularly preferably at an elevated pressure up to 30 bar (absolute) and very particularly preferably at pressures of from 4 to 25 bar (absolute). The temperature in the mixing zone should be at least the melting point of the monophenol, but a reaction temperature in the range from 100° C. to 250° C. is advantageous.

After largely complete mixing of the starting materials, one of the abovementioned catalysts is preferably added, preferably in the preferred amount as solution in the monophenol, to the mixture. Since the catalyzed reaction of monophenol with phosgene to form the aryl ester of chlorocarbonic acid as intermediate proceeds very quickly with elimination of gaseous hydrogen chloride at the abovementioned temperatures and pressures, the reaction can preferably be carried out in a plurality of stages. The reaction can be carried out under adiabatic conditions since it has only a small enthalpy of reaction. In a first stage, viz. the main reactor, predominantly aryl ester of chlorocarbonic acid in addition to further-reacted diaryl carbonate are formed, in particular at elevated pressure and preferably at temperatures of from 120° C. to 230° C., particularly preferably at temperatures of from 130° C. to 210° C., and for the preparation of diphenyl carbonate very particularly preferably at a temperature of from 170° C. to 200° C., and at a reactor liquid residence time of from 15 to 120 minutes, preferably from 45 to 90 minutes. In a second stage, the aryl ester of chlorocarbonic acid reacts in an after-reactor at somewhat higher temperatures of preferably from 170° C. to 250° C., particularly preferably from 190° C. to 230° C. and very particularly preferably from 200° C. to 210° C., at reactor residence times of from 15 to 120 minutes, preferably from 45 to 90 minutes, with monophenol still present to form the diaryl carbonate. Here, the pressure in the second stage in the after-reactor can also be reduced to from 2 to 20 bar. Such a lowering of the pressure can advantageously be carried out in a flash stage, in which the hydrogen chloride gas formed in the main reactor can be separated off particularly readily from the reaction melt as a result of the decreasing pressure. A flash stage for separating off the residual amount of hydrogen chloride can optionally also be present downstream of the second reaction stage in the after-reactor. It can optionally also be integrated into the first distillation column of the subsequent process section III), product purification and catalyst removal by distillation and there accelerate the separation of gas phase and liquid phase.

Continuous reactors are preferably well suited as reactors for the reaction of the starting materials under the indicated reaction conditions, but the use of stirred vessels as batch reactors is also possible. Particularly well-suited continuous reactors are, for example, cascades of stirred vessels, bubble columns, tray columns, packed columns or columns having fixed internals for mixing the reaction medium or reaction distillation columns.

Such columns can also be combined with one another, e.g. a bubble column with a superposed rectification column, in which case, as a deviation from the above-described mixing of the starting materials, the starting materials can be introduced separately at different places on the column combination. Thus, for example, the phosgene can, in the case of the abovementioned column combination, be introduced into the lower bubble column and the monophenol together with the catalyst can be introduced into the upper rectification column having about ten theoretical plates. The diaryl carbonate formed is taken off from the bubble column.

Such a separate introduction of the starting material can also be effected in a reaction distillation column by introducing the phosgene in the middle of the column and introducing the monophenol together with the catalyst at the top of the column. The reaction mixture is taken off form the bottom of the column. Such columns can have at least 5, preferably about 20, plates.

In a further optional embodiment of the reactors, the starting materials can be reacted completely in a main reactor at pressures of from 1 to 25 bar (absolute) at sufficiently high, optionally longer, residence time but lower temperatures in the lower part of the reactor of preferably from 120° C. to 190° C., particularly preferably from 160° C. to 180° C. Additional heating is necessary in the upper part of the reactor in order to achieve somewhat higher temperatures up to 250° C., preferably up to 230° C., there. The substantial degassing of the reaction mixture and removal of the low boilers can subsequently be carried out by means of flash evaporation or another degassing technique.

Particular preference is given to bubble columns through which the starting material mixture as described above is passed from the bottom upward. Here, the gaseous hydrogen chloride is taken off at the top of the bubble column and the reaction mixture is taken off at the upper end of the shaft of the column. This is fed to the next bubble column, which functions as after-reactor, via the bottom of the column. The fully reacted reaction mixture is taken off from the last bubble column at the end of a residence reactor and fed to the subsequent process section III), product purification and removal of catalyst by distillation. The hydrogen chloride gas taken off in each case at the top of the bubble columns is purified in the subsequent process section II), viz. the hydrogen chloride work-up. Additional removal of hydrogen chloride is also possible between the individual stages by the depressurization in a flash vessel and a subsequent increase in pressure.

The apparatus materials have to meet the demanding requirements in respect of resistance to hydrogen chloride and phosgene at high temperatures and are preferably selected from the group of materials black steel, stainless steel, steel alloys, nickel-based alloys (e.g. Hastelloy C), ceramic, graphite, enamel-coated materials, PTFE-clad materials.

The objective of the optional process section II), viz. the hydrogen chloride work-up, is the isolation and purification of the by-product hydrogen chloride. For this purpose, the gas phase formed in the reaction A) is collected and the hydrogen chloride gas is separated from the other components which can optionally be recirculated for a further reaction to form diaryl carbonate. The by-product hydrogen chloride can be distilled to increase the purity. Furthermore, the gaseous substream from process section III) can be added.

In this process section II), the HCl-containing streams from process section I) are combined and purified jointly. The hydrogen chloride is preferably not neutralized. The main product among the low-boiling components is, with a proportion of 94% by weight or more, the hydrogen chloride gas; by-products are the monophenol which has been used in excess in a proportion of more than 3% by weight and traces of aryl ester of chlorocarbonic acid, diaryl carbonate and phosgene and, as by-product from the phosgene, traces of carbon monoxide and carbon tetrachloride. The by-products can be largely separated by means of various steps from the main product hydrogen chloride, so that a hydrogen chloride gas having a purity of more than 99.0% by volume, preferably more than 99.8% by volume, and a residual content of phosgene and/or chlorocarbonic esters of less than 1000 ppm by volume, preferably less than 500 ppm by volume, is obtained. The content of organic compounds in the hydrogen chloride should likewise be less than 1000 ppm by volume, preferably less than 50 ppm by volume; in particular, the content of chlorine-containing hydrocarbons should be less than 50 ppm by volume.

This object is achieved by one or more steps which are described below. This object is preferably achieved by a multistage process. The hydrogen chloride is preferably separated off by distillation.

In a first condensation stage, the by-products having a boiling point higher than that of hydrogen chloride are partially condensed out at a suitable temperature. Here, relatively high-boiling components which are present in a relatively high concentration, e.g. monophenols and diaryl carbonates, are, in particular, largely removed from the hydrogen chloride gas and recirculated to the reaction. This separation is particularly successful when elevated pressures are optionally also employed in addition to the relatively low temperature. Preferred temperatures in the first condensation stage are at least 80° C., and for the preparation of diphenyl carbonate particularly preferably 90° C. The pressure is preferably set in the range from 8 to 25 bar (absolute), and a particularly preferred pressure for the preparation of diphenyl carbonate is 12 bar (absolute). The condensation of the by-products from the hydrogen chloride gas stream can optionally also be carried out in a plurality of stages at various temperatures and/or pressures.

If a sufficiently low temperature or a sufficiently high pressure is technically impossible or difficult to achieve, this first condensation stage can also be circumvented in order to scrub out the by-products from the hydrogen chloride stream in a subsequent HCl scrubbing stage in a suitable apparatus using molten diaryl carbonate. If this HCl scrubbing stage is the first purification stage for the hydrogen chloride, circumventing the first condensation stage, this HCl scrubbing stage can also comprise a plurality of stages and be operated at various, decreasing temperature levels in order to increase the efficiency of the scrub. Here, monophenols in particular are very readily soluble in the diaryl carbonate. Traces of chlorocarbonic ester and phosgene can also be reacted to form the diaryl carbonate in this process step when the diaryl carbonate used for the scrub is, for example, taken off at a suitable place in the subsequent process section C), viz. the diaryl carbonate work-up. In principle, any diaryl carbonate stream from this process section through to the distilled diaryl carbonate is suitable for the HCl scrubbing stage, and it can be advantageous for the reaction of the abovementioned organic chlorine compounds to take off a catalyst- and phenol-containing diaryl carbonate stream for the HCl scrubbing stage from the process section III) in order to be able to react the organic chlorine compounds still present in the hydrogen chloride gas in a short time.

One such suitable diaryl carbonate is the crude diaryl carbonate which leaves the process section I) (reaction) and is fed for further work-up into the first stage of the process section III) (diaryl carbonate work-up). Sufficient amounts of catalyst and of monophenol are present in this diaryl carbonate. As an alternative, a distilled diaryl carbonate can be used in any way for the HCl scrubbing stage since the physical solubility of the by-products to be scrubbed out in the DPC is sufficiently high. However, a pure distilled diaryl carbonate is preferably used for the HCl scrubbing stage. To react the organic chlorine compounds in the HCl scrubbing stage, it is possible to use the monophenol instead of the diaryl carbonate as scrubbing medium since the physical solubility of the by-products to be scrubbed out in the monophenol is also sufficiently high. This monophenol can be, for example, a substream of the monophenol feed stream. If a reaction of chloro esters or phosgene to form diaryl carbonate is desired, the monophenol used for the scrub can contain catalyst in any way. The HCl scrub using diaryl carbonate or using monophenol is preferably carried out at temperatures above the melting point of the diaryl carbonate; in the preparation of diphenyl carbonate, a melt temperature of 80-95° C. is particularly preferred. The HCl scrub can be carried out at atmospheric pressure or at an elevated pressure of from 8 to 25 bar (absolute); in the preparation of diphenyl carbonate, 12 bar (absolute) is particularly preferred.

In such a scrub, a hydrogen chloride gas having a purity of more than 99.8% by weight can be obtained. The proportion of phosgene is preferably below 500 ppm by volume, and that of chloroformic ester is preferably reduced to below the detection limit and the phenol content is preferably reduced to below 10 ppm by volume.

This HCl scrubbing stage is not absolutely necessary and can also be circumvented in the case of any combination of other process steps with one another.

A hydrogen chloride distillation is particularly well suited for achieving high purities of the hydrogen chloride gas. In order to be able to carry out such a distillation in an energy-efficient manner, prior cooling of the hydrogen chloride to be purified to relatively low temperatures in a preceding second condensation stage is useful, but not absolutely necessary. If this stage is omitted, then a correspondingly greater quantity of energy at low temperatures is necessary in the subsequent hydrogen chloride distillation. In this second condensation stage, which can optionally also operate at a number of different temperature and/or pressure levels, the traces of relatively high-boiling byproducts still present in the hydrogen chloride gas are separated out, in particular when relatively high pressures in the range from 8 to 25 bar (absolute), in the case of diphenyl carbonate preferably 12 bar (absolute), are employed. The temperatures can vary as a function of the technical circumstances in a very wide range from plus 25° C. to minus 50° C. This second condensation stage is, in particular, very advisable when the scrub in the HCl scrubbing stage has been carried out using monophenol, since the concentration of monophenol present in the HCl gas stream can be significantly decreased in this way and the load in the HCl distillation is thus decreased. If this second condensation stage is omitted, the energy requirements in the HCl distillation are correspondingly very much higher. The condensates can likewise, as in the first condensation stage, be fed to the reaction.

As fourth and last stage of the hydrogen chloride work-up in process section II), the distillation of hydrogen chloride is, in a particularly preferred embodiment, particularly well suited for the preparation of a high-purity hydrogen chloride. It should preferably be carried out at elevated pressure since otherwise the energy consumption for setting sufficiently low temperatures which would alternatively be required would be disproportionately high. Should preceding purification stages have been carried out under atmospheric pressure, compression of the hydrogen chloride stream to relatively high pressures of from 8 to 25 bar (absolute) at the latest in this purification stage is very advisable; for the preparation of diphenyl carbonate, 12 bar (absolute) is particularly preferred. A hydrogen chloride gas having a purity of 99.95% by weight is obtainable under these conditions.

All the four abovementioned stages of the hydrogen chloride purification in process section II) are, in the order described, particularly well suited according to the invention for the preparation of a high-purity hydrogen chloride gas. Adherence to particular orders or the implementation of all process stages is not absolutely necessary but instead depends on the degree of contamination of the hydrogen chloride separated off from the reaction and on the desired purity of the hydrogen chloride gas as end product. Thus, it may be quite possible to achieve the desired result using individual purification stages or a single purification stage, as illustrated below for the example of the HCl distillation.

If the feed streams from the process section I) (reaction) are fed directly without prior purification to the hydrogen chloride distillation, a hydrogen chloride gas having a purity of 99.95% by weight is likewise obtainable under the same temperature and pressure conditions.

A combination of the purification stages can quite possibly be carried out in a particular order independent of the abovementioned enumeration in order to achieve particular purities.

As apparatuses for carrying out the first and second condensation stages, classical cold traps having a heat transfer surface area which is sufficiently high for the process conditions and an apparatus for feeding the condensate into the reaction are suitable. Such cold traps can also be configured with a plurality of stages and can optionally be maintained at different temperatures. Suitable apparatuses for the HCl scrubbing stage are, in particular, continuously operated apparatuses such as bubble columns, bubble cap tray columns, columns containing random packing, columns containing ordered packing, columns having fixed intemrnals, in which the scrubbing liquid can be conveyed from the top in countercurrent to the ascending hydrogen chloride gas. Continuously operated stirred apparatuses, e.g. mixer-settlers, or else discontinuously operated stirred apparatuses are in principle also suitable.

The hydrogen chloride distillation can be carried out in conventional distillation or rectification columns having suitable column internals.

The materials for the abovementioned apparatuses have to meet the demanding requirements in respect of resistance to hydrogen chloride and are preferably selected from the group black steel, stainless steel, steel alloys, nickel-based alloys (e.g. Hastelloy C), ceramic, graphite, enamel-coated materials, PTFE-clad materials.

In process section III), viz. product purification and catalyst removal, the relatively high-boiling components formed in the reaction I) are collected, separated and the catalyst is recirculated in the form of the free base or in the form of the hydrochloride to the reaction. The main product is thus purified to such an extent that a diaryl carbonate having a purity of more than 99.0% by weight, preferably more than 99.8% by weight, particularly preferably more than 99.95% by weight, is obtained.

It has surprisingly been discovered that isolation and recirculation of the catalyst from the reaction mixture is possible by means of distillation without desublimation of the catalyst occurring.

Figure 1:
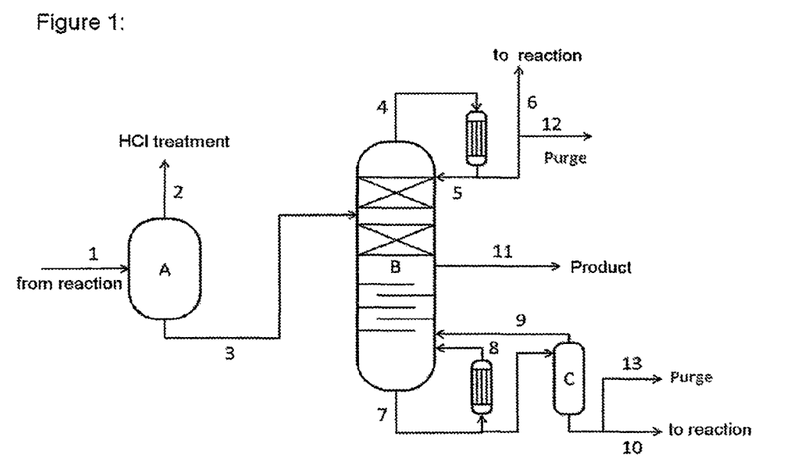
FIG. 1 is a process flow diagram showing the isolation and recirculation of the catalyst from a reaction mixture by distillation without desublimation of the catalyst.

A pictorial overview of this process section is shown in FIG. 1.

In a first separation step for the liquid reaction mixture, dissolved hydrogen chloride is largely separated off in a degassing stage. This can be effected by means of a flash vessel (A in FIG. 1), a distillation column, a combination of these apparatuses or a further conventional degassing technique (e.g. stripping).

Preference is given to using a flash stage (A), in which the dissolved hydrogen chloride is outgassed by lowering the pressure. Pressures of from 20 mbar to 1 bar (absolute) and temperatures of 140°-205° C. are chosen here, preferably pressures of from 0.1 bar to 1 bar (absolute) and temperatures of 165-205° C. and particularly preferably pressures of 0.3-0.7 bar (absolute) and temperatures of 180-200° C.

As an alternative, the removal of hydrogen chloride can be carried out using a distillation column which is operated at pressures of from 200 mbar to 2 bar (absolute), preferably from 0.5 to 1 bar (absolute), particularly preferably 0.8-1 bar (absolute).

A mixture of hydrogen chloride, monophenol and free, optionally substituted pyridine is obtained in the vapor phase of the flash vessel or at the top of the alternative distillation column. This mixture is preferably added to the main gas stream for gas work-up in process section B).

The bottoms from the flash vessel or the alternative column are largely free of hydrogen chloride and, in the preferred variant, low in monophenol. The bottoms are thus composed of diaryl carbonate, monophenol, optionally substituted pyridine, in free form and in the form of the hydrochloride, and by-products.

In further variants, flash stages and distillation columns can be combined for separating off hydrogen chloride or a further degassing technique (e.g. stripping) can be used. As an alternative, the first separation step can also be omitted. However, this is not preferred because larger process streams for the second separation step are obtained in this way and the hydrogen chloride carried over into the further separation stages can cause corrosion problems.

In the second separation step, diaryl carbonate is isolated from the prepurified stream from the first separation step (stream 3 in FIG. 1) by separating off monophenol, pyridine hydrochloride and secondary components. It has been found in experiments that the vapor-liquid equilibrium of a binary mixture consisting of diaryl carbonate and pyridine hydrochloride displays heteroazeotropic behavior (see FIG. 2). A minimum azeotrope is found at a proportion by mass of 85% by weight of pyridine-HCl. The liquid separates into a pyridine hydrochloride-containing phase and a diaryl carbonate-containing phase. Separation of the pyridine hydrochloride from the diaryl carbonate by means of a separation technique whose principle is based on the vapor-liquid equilibrium, e.g. distillation, therefore appears to be made difficult. Furthermore, the high melting point of pyridine hydrochloride of 140-146° C. can be a hindrance in a distillation since resublimation in the condenser can lead to operational problems.

Surprisingly, the feasibility of separation of diaryl carbonate from phenol, pyridine hydrochloride and secondary components by distillation has been confirmed in experiments.

In the preferred variant, diaryl carbonate purified in the second separation step is therefore obtained as side stream (11) from a distillation column (see FIG. 1). The monophenol, free pyridine, pyridine hydrochloride and low-boiling secondary components are taken off in the distillate. Owing to the azeotrope of diaryl carbonate and pyridine hydrochloride, the distillate also has a proportion of about 5-15% by weight of diaryl carbonate.

The high-boiling secondary components and thermal decomposition products are taken off at the bottom. In order for product-damaging temperatures of 220° C. not to be exceeded at the bottom of the column and the bottoms to remain pumpable, a proportion of diaryl carbonate of 10-50% by weight, particularly preferably 20-40% by weight, is preferably left in the bottoms.

A pressure of 5-100 mbar (absolute), particularly preferably 10-40 mbar (absolute), is preferably set at the top of the distillation column. The temperature at the top ranges from 60° C. to 140° C. as a function of the pressure at the top, the excess of monophenol and the catalyst concentration in the reaction. At the bottom, temperatures of 180-250° C., preferably 200-220° C. prevail. As a result of these high temperatures at the bottom, the proportion of the secondary component Salol is reduced by thermal decomposition. A diaryl carbonate having a purity of more than 99% by weight can thus be obtained in the side stream. The side stream is preferably taken off from the vapor phase, but can also be taken off from the liquid phase.

The purity of the diaryl carbonate in the side stream can be increased further by use of a side column. However, the distillation column is preferably operated in such a way that the side stream can be introduced without further purification into the subsequent process steps, e.g. into the melt polycarbonate process.

The distillate is recirculated to the reaction. Part of the distillate is preferably discharged as purge in order to discharge low-boiling secondary components. The bottom product is disposed of or, in a preferred variant, recirculated after removal of a high boiler purge stream to the reaction. In a particularly preferred variant, part of the diaryl carbonate present in the bottoms is separated off under mild conditions in a further separation operation (C in FIG. 1), e.g. a thin film evaporator, and returned to the distillation column in order to reduce the proportion of diaryl carbonate in the high boiler purge.

Figure 3:
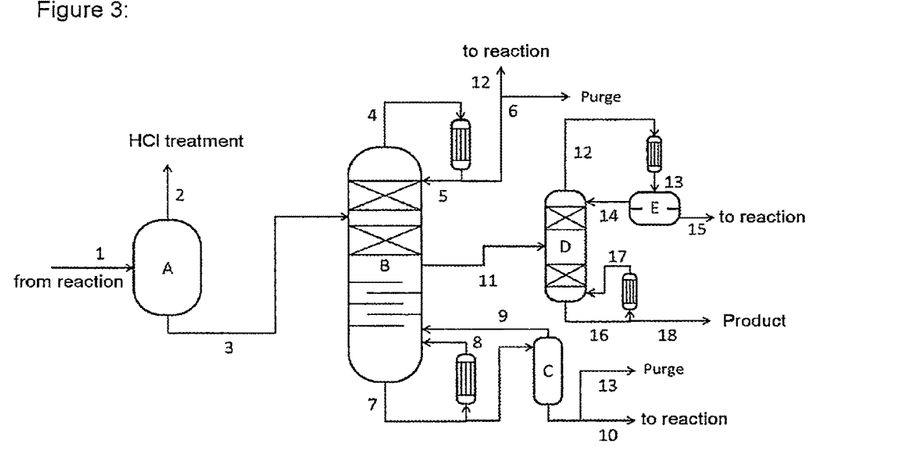
FIG. 3 is a process flow diagram showing the isolation and recirculation of the catalyst from a reaction mixture by distillation without desublimation of the catalyst.

An alternative variant to the above-described preferred distillation provides for taking-off of a mixture consisting of diaryl carbonate and pyridine hydrochloride in a side stream of a distillation column (see FIG. 3). In an additional distillation column, pure diaryl carbonate is then obtained from this mixture at the bottom.

At the top of the first distillation column of the alternative variant (B in FIG. 3), phenol and low-boiling secondary components are taken off at a pressure at the top of 5-100 mbar (absolute), preferably 10-40 mbar (absolute), and a temperature at the top of 60-115° C. The composition and temperature of the bottoms resemble those of the bottoms in the above-described preferred variant of the distillation column. The distillate and the bottom product are recirculated to the reaction, as in the above-described preferred variant.

The additional distillation column for purifying the side stream (D in FIG. 3) in the alternative variant is preferably configured as a heteroazeotropic distillation. A decanter at the top (E in FIG. 3) separates the distillate into a diaryl carbonate-rich phase and a pyridine hydrochloride-rich phase. The pyridine hydrochloride-rich phase is taken off as overhead product and recirculated to the reaction. The diaryl carbonate-rich phase is returned as runback to the column. In order to increase the runback, a mixture of both phases from the decanter can also be recirculated to the column. Diaryl carbonate having a purity of more than 99% by weight is obtained at the bottom of the column and can be passed without further purification to the subsequent process steps, e.g. the melt polycarbonate process.

EXPLANATIONS OF THE FIGURES

FIG. 1 shows a preferred embodiment of process section III), viz. product purification and catalyst removal by distillation.

Figure 2:
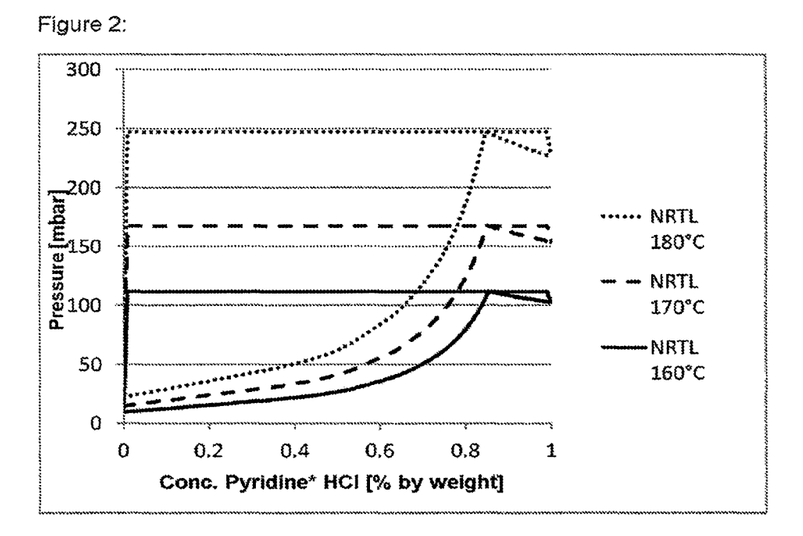
FIG. 2 is a graph showing experimentally determined vapor-liquid-liquid equilibria for diphenyl carbonate/pyridine hydrochloride mixtures as a function of pressure at various temperatures.

FIG. 2 shows the experimentally determined vapor-liquid-liquid equilibrium of diphenyl carbonate/pyridine hydrochloride mixtures as a function of the pressure at various temperatures (160° C., 170° C. and 180° C.). This displays a minimum azeotrope at a proportion by mass of 85% by weight of pyridine hydrochloride.

FIG. 3 describes a further preferred embodiment of process section III), viz. product purification and catalyst removal by distillation.

EXPLANATIONS FOR FIGS. 1 AND 3

A: Flash stage
B: Distillation column
C: Additional separation operation (e.g. thin film evaporator)
D: Side stream distillation column
E: Decanter
1: Reaction mixture
2: Vapor from flash stage
3: Bottoms from flash stage
4: Vapor from distillation column
5: Runback to distillation
6: Recirculation of the distillate to the reaction
7: Bottoms from distillation column
8: Vaporizer vapor into distillation column
9: Vapor from additional separation operation (e.g. thin film evaporator) into distillation column
10: Recirculation of the bottoms to the reaction
11: Product stream (DPC)
12: Purge to remove low-boiling secondary components
13: Purge to remove high-boiling secondary components The following examples are intended to illustrate the procedure for making the removal of pyridine hydrochloride by distillation feasible, but without constituting any restrictions.

EXAMPLES

Various mixtures of diphenyl carbonate (DPC), phenol, pyridine hydrochloride (pyridinium chloride, hereinafter also referred to as "pyridine.HCl" or "PyHCl") and Salol (phenyl salicylate, by-product of the direct phosgenation of phenol) are introduced into a laboratory distillation apparatus consisting of a distillation flask (1 l) provided with a 30 cm long Vigreux column (wrapped in aluminum foil for insulation), a Liebig condenser (operated at 80° C. using warm water), a cold trap (at −80° C.) and a vacuum pump. The temperature at the top and bottom of the column is measured. The molten mixture is in each case fractionally distilled at about 20 mbar (absolute). The 2 or 3 fractions are collected separately and, like the bottoms and the contents of the cold trap, analyzed by gas chromatography.

Example 1

The following synthetic reaction mixture is distilled in the apparatus described:

|  | Mass [g] | Composition [% by wt.] | Molar amount [mol] |  |
|---|---|---|---|---|
| Phenol | 70.5 | 17.6 | 0.75 | Feed |
| Pyridine | 5.68 | 1.4 | 0.072 |  |
| HCl | 2.96 | 0.7 | 0.081 |  |
| DPC | 319.6 | 79.9 | 1.49 |  |
| Salol | 1.28 | 0.3 | 0.01 |  |
| Total | 400 | 100 | — |  |

The following fractions are formed in the distillation:

|  | Mass [g] | Temperature at the top [° C.] | Pressure (absolute) [mbar] | State of matter at room temperature |
|---|---|---|---|---|
| Fraction 1 | 55.7 | 80-82 | 21 | Solid |
| Fraction 2 | 26 | 118-134 | 21 | Liquid |
| Fraction 3 | 95 | 175-193 | 21 | Solid |
| Residue | 219.4 | — | 21 | Solid |
| Cold trap | 0.2 | — | — | — |
| Total | 396 |  |  |  |

Astonishingly, fraction 2 is liquid at room temperature and also remains this way permanently.

Analysis of the individual fractions gives the following compositions (the deviations of the totals of the compositions from 100% are due to measurement inaccuracies):

|  | Mass [g] | Composition [% by wt.] | Molar amount [mol] |  |
|---|---|---|---|---|
| Phenol | 55.70 | 100.0 | 0.5926 | Fraction 1 |
| Pyridine | 0.04 | 0.1 | 0.001 |  |
| HCl | 0.02 | 0.0 | 0.001 |  |
| DPC | 0.40 | 0.7 | 0.0019 |  |
| Salol | 0.00 | 0.0 | 0.0000 |  |
| Total | 55.7 | 101 | — |  |
| Phenol | 12.30 | 47.31 | 0.1309 | Fraction 2 |
| Pyridine | 5.28 | 20.31 | 0.0668 |  |
| HCl | 2.54 | 9.77 | 0.0697 |  |
| DPC | 3.50 | 13.46 | 0.0164 |  |
| Salol | 0.01 | 0.05 | 0.0001 |  |
| Total | 26.0 | 91 | — |  |
| Phenol | 0.40 | 0.42 | 0.0043 | Fraction 3 |
| Pyridine | 0.13 | 0.14 | 0.0016 |  |
| HCl | 0.04 | 0.04 | 0.0011 |  |
| DPC | 95.00 | 100.00 | 0.4439 |  |
| Salol | 0.23 | 0.25 | 0.0011 |  |
| Total | 95.0 | 101 | — |  |
| Phenol | 0.06 | 0.03 | 0.0006 | Bottoms |
| Pyridine | 0.00 | 0.00 | 0.0000 |  |
| HCl | 0.00 | 0.00 | 0.0000 |  |
| DPC | 208.00 | 94.80 | 0.9720 |  |
| Salol | 0.48 | 0.22 | 0.0023 |  |
| Total | 219.4 | 95 | — |  |
| Phenol |  | 0.00 | 0.0000 | Cold trap |
| Pyridine |  | 0.00 | 0.0000 |  |
| HCl | 0.04 | 20.00 | 0.0011 |  |
| DPC |  | 0.00 | 0.0000 |  |
| Salol |  | 0.00 | 0.0000 |  |
| Total | 0.20 | 20 | — |  |

It is conspicuous that the molar ratio of pyridine to HCl in the individual fractions is in each case about 1:1. The distillation bottoms, on the other hand, are free of pyridine hydrochloride. In the cold trap, small amounts of HCl are recovered, but there are no signs of deposition of pyridine hydrochloride as salt. This indicates that pyridine hydrochloride can surprisingly be distilled off as salt as low boiler from a crude diphenyl carbonate (DPC) reaction mixture.

Example 2

The following synthetic reaction mixture is distilled in the apparatus described:

|  | Mass [g] | Composition [% by wt.] | Molar amount [mol] | |
|---|---|---|---|---|
| Phenol | 28 | 7.0 | 0.30 | Feed |
| Pyridine | 13.12 | 3.3 | 0.166 | |
| HCl | 6.08 | 1.5 | 0.167 | |
| DPC | 351.6 | 87.9 | 1.64 | |
| Salol | 1.2 | 0.3 | 0.01 | |
| Total | 400 | 100 | — | |

The following fractions are formed in the distillation column:

|  | Mass [g] | Temperature at the top [° C.] | Pressure (absolute) [mbar] | State of matter at room temperature |
|---|---|---|---|---|
| Fraction 1 | 0 | — | — | — |
| Fraction 2 | 52.3 | 115-130 | 20 | Liquid |
| Fraction 3 | 98.1 | 175-178 | 20 | Solid |
| Residue | 247.1 | — | 20 | Solid |
| Cold trap | 0.3 | — | 20 | Liquid, acidic |
| Total | 397.8 | | | |

Owing to the significantly lower proportion of phenol, the first fraction consisting predominantly of phenol does not occur, in contrast to example 1. The other observations, in particular the fraction 2 which is liquid at room temperature, also apply in the case of example 2.

Analysis of the individual fractions gives the following compositions (the deviations of the totals of the compositions from 100% are due to measurement inaccuracies):

|  | Mass [g] | Composition [% by wt.] | Molar amount [mol] | |
|---|---|---|---|---|
| Phenol | | | | Fraction 1 |
| Pyridine | | | | (nonexistent) |
| HCl | | | | |
| DPC | | | | |
| Salol | | | | |
| Total | 0.0 | | — | |

|  | Mass [g] | Composition [% by wt.] | Molar amount [mol] | |
|---|---|---|---|---|
| Phenol | 29.70 | 56.79 | 0.3160 | Fraction 2 |
| Pyridine | 14.20 | 27.15 | 0.1795 | |
| HCl | 5.05 | 9.66 | 0.1385 | |
| DPC | 6.60 | 12.62 | 0.0308 | |
| Salol | 0.24 | 0.46 | 0.0011 | |
| Total | 52.3 | 107 | — | |
| Phenol | 0.40 | 0.41 | 0.0043 | Fraction 3 |
| Pyridine | 0.14 | 0.14 | 0.0018 | |
| HCl | 0.07 | 0.07 | 0.0019 | |
| DPC | 96.00 | 97.86 | 0.4486 | |
| Salol | 0.24 | 0.24 | 0.0011 | |
| Total | 98.1 | 99 | — | |
| Phenol | 0.11 | 0.04 | 0.0012 | Residue |
| Pyridine | 0.04 | 0.02 | 0.0005 | |
| HCl | 0.00 | 0.00 | 0.0001 | |
| DPC | 243.10 | 98.38 | 1.1360 | |
| Salol | 0.49 | 0.20 | 0.0023 | |
| Total | 247.1 | 99 | — | |
| Phenol | | 0.00 | 0.0000 | Cold trap |
| Pyridine | | 0.00 | 0.0000 | |
| HCl | 0.05 | 16.67 | 0.0014 | |
| DPC | | 0.00 | 0.0000 | |
| Salol | | 0.00 | 0.0000 | |
| Total | 0.30 | 17 | — | |

It is again conspicuous that, in particular in fraction 2 in which the main part of the pyridine hydrochloride salt used is recovered, the molar ratio of pyridine to HCl is virtually ideally 1:1. The distillation bottoms are again free of pyridine hydrochloride. Once again, small amounts of HCl are recovered in the cold trap, but in this experiment, too, there are no signs of deposition of the pyridine hydrochloride as salt. It is thus confirmed that pyridine hydrochloride can surprisingly be distilled off as salt as low boiler from a crude diphenyl carbonate (DPC) reaction mixture.

Comparative Example 1

As comparative example, the following mixture of pyridine hydrochloride (contains traces of water) is distilled:

|  | Mass [g] | Composition [% by wt.] | Molar amount [mol] | |
|---|---|---|---|---|
| Pyridine | 135.4 | 67.7 | 1.712 | Feed |
| HCl | 62.6 | 31.3 | 1.717 | |
| $H_2O$ | 2 | 1.0 | 0.11 | |
| Total | 200 | 100 | — | |

The following fractions are formed in the distillation:

|  | Mass [g] | Temperature at the top [° C.] | Pressure (absolute) [mbar] | State of matter at room temperature |
|---|---|---|---|---|
| Fraction 1 | 5.4 | 52 | 20 | Liquid |
| Fraction 2 | 10 | 137 | 20 | Solid |
| Residue | 166.6 | — | 20 | Solid |
| Cold trap | 1.3 | — | 20 | Liquid, acidic |
| Total | 183.3 | | | |

Analysis of the individual fractions gives the following compositions (the deviations of the totals of the compositions from 100% are due to measurement inaccuracies):

|  | Mass [g] | Composition [% by wt.] | Molar amount [mol] |  |
|---|---|---|---|---|
| Pyridine | 5.40 | 100.00 |  | Fraction 1 |
| HCl | 0.11 | 2.04 |  |  |
| H2O |  | 0.00 |  |  |
| Total | 5.4 | 102 | — |  |
| Pyridine | 7.80 | 78.00 | 0.0986 | Fraction 2 |
| HCl | 3.25 | 32.50 | 0.0891 |  |
| H2O |  |  |  |  |
| Total | 10.0 | 111 | — |  |
| Pyridine | 116.60 | 69.99 | 1.4741 | Residue |
| HCl | 49.10 | 29.47 | 1.3467 |  |
| H2O |  |  |  |  |
| Total | 166.6 | 99 | — |  |
| Pyridine |  | 0.00 | 0.0000 | Cold trap |
| HCl | 0.23 | 17.69 | 0.0063 |  |
| H2O |  |  |  |  |
| Total | 1.3 | 18 | — |  |

On heating pure pyridine hydrochloride, too, virtually no dissociation of the salt occurs at the selected temperature. Only in fraction 1, the temperature, the state of matter at room temperature and also the composition indicate elimination of pure pyridine.

In fraction 2, small amounts of pyridine-HCl in an approximately 1:1 composition are found.

The predominant part of the pyridine hydrochloride salt remains, as expected, in the bottom of the column. Small amounts of HCl are again recovered in the cold trap, but there are no signs of deposition of pyridine hydrochloride as salt in this experiment, too.

Comparative Example 2

A synthetic mixture of 40% by weight of pyridine hydrochloride and 60% by weight of phenol (analogous to fraction 2 from examples 1 and 2) is produced. The mixture is liquid at room temperature.

The lowering of the freezing point of the pyridine hydrochloride dissolved in phenol results in the mixture occurring in the distillation also being liquid and no desublimation in vacuum lines, etc., therefore being expected in an industrial distillation apparatus, too.

The invention claimed is:

1. A process for preparing diaryl carbonate comprising:
   a. reacting at least one monophenol with phosgene and/or at least one aryl chloroformate in the presence of at least one optionally substituted pyridine, in free form and/or in the form of a hydrochloride salt thereof, as catalyst, wherein the reaction is carried out in a reactor under pressures of 1-50 bar (absolute),
   b. transferring the reaction mixture from the reactor into a single-stage distillation apparatus or a multistage distillation apparatus,
   c. separating a catalyst-containing distillate off at the top of at least one distillation column,
   d. at least partially recirculating the catalyst-containing distillate into the reactor at step a), and
   e. separating diaryl carbonate off via a side stream from the distillation apparatus, wherein an aqueous solution is not used in any of the steps a) to e).

2. The process as claimed in claim 1, wherein the at least one monophenol comprises phenol.

3. The process as claimed in claim 1, wherein not more than 10 mol % of the optionally substituted pyridine is present in free form.

4. The process as claimed in claim 3, wherein the catalyst comprises pyridine hydrochloride.

5. The process as claimed in claim 1, wherein hydrogen chloride formed in step a) is not neutralized.

6. The process as claimed in claim 1, wherein hydrogen chloride formed in step a) is separated off by distillation in a first distillation stage and the catalyst-containing distillate and the diaryl carbonate-containing side stream are separated off in a further distillation stage.

7. The process as claimed in claim 1, further comprising:
   taking off as a side stream from the distillation apparatus a mixture comprising—at least part of the optionally substituted pyridine in the form of the hydrochloride and diaryl carbonate; and
   fractionating the side stream in a separate heteroazeotropic distillation, wherein the diaryl carbonate is separated off as a bottom product.

8. The process as claimed in claim 1, further comprising further purifying the diaryl carbonate separated off via the side stream from the distillation apparatus.

9. The process as claimed in claim 1, wherein not more than 1 mol % of the optionally substituted pyridine is present in free form.

10. The process as claimed in claim 1, wherein the at least one monophenol consists essentially of phenol.

11. The process as claimed in claim 3, wherein the catalyst consists essentially of pyridine hydrochloride.

* * * * *